US008779093B2

United States Patent
Leveillard et al.

(10) Patent No.: US 8,779,093 B2
(45) Date of Patent: Jul. 15, 2014

(54) NEURONAL VIABILITY FACTOR AND USE THEREOF

(75) Inventors: Thierry Leveillard, Charenton (FR); Celine Jaillard, Paris (FR); Jose-Alain Sahel, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 352 days.

(21) Appl. No.: 13/062,035

(22) PCT Filed: Sep. 10, 2009

(86) PCT No.: PCT/EP2009/061764
§ 371 (c)(1),
(2), (4) Date: Aug. 9, 2011

(87) PCT Pub. No.: WO2010/029130
PCT Pub. Date: Mar. 18, 2010

(65) Prior Publication Data
US 2012/0245093 A1    Sep. 27, 2012

(30) Foreign Application Priority Data
Sep. 10, 2008 (EP) .................................... 08305541

(51) Int. Cl.
*C07K 2/00* (2006.01)
*C07K 4/00* (2006.01)
*C07K 5/00* (2006.01)
*C07K 7/00* (2006.01)
*C07K 14/00* (2006.01)
*A61K 38/00* (2006.01)
*A61K 38/18* (2006.01)
*C07K 14/475* (2006.01)
*C07K 14/48* (2006.01)

(52) U.S. Cl.
USPC ............. 530/350; 530/300; 530/324; 436/89; 514/7.6; 514/8.3; 514/8.4

(58) Field of Classification Search
None
See application file for complete search history.

(56) References Cited

U.S. PATENT DOCUMENTS 7,795,387 B2 * 9/2010 Leveillard et al. ............ 530/350

FOREIGN PATENT DOCUMENTS

WO    02/081513    10/2002
WO    2005/113586    12/2005

OTHER PUBLICATIONS

Fu et al. EMBO Journal, 1996, vol. 15, pp. 4392-4401.*
Bowie et al. Science, 1990, 257:1306-1310.*
Bork. Genome Research, 2000,10:398-400.*
Nature Genetics, 1999, 21:440-443.*
Gustafsson, J. A.. Eur J Cancer. Sep. 2000;36 Suppl 4:S16.*
Burgess et al. J of Cell Bio. 111:2129-2138, 1990.*
Pawson et al. 2003, Science 300:445-45.*
International Search Report in PCT/EP09/61764, dated Oct. 22, 2009.
Chalmel et al., BMC Mol. Biol., 8:74 (2007).

* cited by examiner

*Primary Examiner* — Chang-Yu Wang
(74) *Attorney, Agent, or Firm* — McAndrews, Held & Malloy Ltd.

(57) ABSTRACT

This invention relates to methods and compositions for detection and treatment of neurodegenerative diseases. In particular, the invention relates to polypeptides that can protect against neuron degeneration, nucleic acid molecules that encode such polypeptides, and antibodies that recognize said polypeptides.

5 Claims, No Drawings

NEURONAL VIABILITY FACTOR AND USE THEREOF

The present application is filed pursuant to 35 U.S.C. 371 as a U.S. National Phase application of International Patent Application No. PCT/EP09/61764, which was filed Sep. 10, 2009, claiming the benefit of priority to European Patent Application No. 08305541.8, which was filed on Sep. 10, 2008. The entire text of the aforementioned applications is incorporated herein by reference in its entirety.

FIELD OF THE INVENTION

This invention relates to methods and compositions for detection and treatment of neurodegenerative diseases. In particular, the invention relates to polypeptides that can protect against neuron degeneration, nucleic acid molecules that encode such polypeptides, and antibodies that recognize said polypeptides.

BACKGROUND OF THE INVENTION

Neurodegenerative disorder encompasses a range of seriously debilitating conditions that are characterized by neuron degeneration.

As an example of such a neurodegenerative disorder, retinitis pigmentosa (RP) is a genetically heterogeneous retinal degeneration characterized by the sequential degeneration of a population of neurons corresponding to rod and cone photoreceptors.

Photoreceptors are a specialized subset of retinal neurons that are responsible for vision. Photoreceptors consist of rods and cones which are the photosensitive cells of the retina. Each rod and cone elaborates a specialized cilium, referred to as an outer segment that houses the phototransduction machinery. The rods contain a specific light-absorbing visual pigment, rhodopsin. There are three classes of cones in humans, characterized by the expression of distinct visual pigments: the blue cone, green cone and red cone pigments. Each type of visual pigment protein is tuned to absorb light maximally at different wavelengths. The rod rhodopsin mediates scotopic vision (in dim light), whereas the cone pigments are responsible for photopic vision (in bright light). The red, blue and green pigments also form the basis of color vision in humans. The visual pigments in rods and cones respond to light and generate an action potential in the output cells, the rod bipolar neurons, which is then relayed by the retinal ganglion neurons to produce a visual stimulus in the visual cortex.

In humans, a number of diseases of the retina involve the progressive degeneration and eventual death of photoreceptors, leading inexorably to blindness. Degeneration of photoreceptors, such as by inherited retinal dystrophies (e.g., retinal degenerative disorders), age related macular degeneration and other maculopathies, or retinal detachment, are all characterized by the progressive atrophy and loss of function of photoreceptor outer segments. In addition, death of photoreceptors or loss of photoreceptor function results in partial differentiation of second order retinal neurons (rod bipolar cells and horizontal cells) in patients with retinal dystrophies, thereby decreasing the overall efficiency of the propagation of the electrical signal generated by photoreceptors. Secondary glial and pigment epithelium changes secondary to photoreceptors degeneration result in vascular changes leading to ischemia and gliosis.

Trophic factors that are capable of rescuing photoreceptors from cell death and/or restoring the function of dysfunctional (atrophic or dystrophic) photoreceptors may represent useful therapies for the treatment of such conditions. For example, document WO02081513 has described the use of the Rod-derived Cone Viability Factor 1 and 2 (RdCVF1 and RdCVF2) for the treatment of retinal degenerative disorders. The RdCVF gene, also called thioredoxin-like 6 (Txnl6) and more recently Nucleoredoxin like (Nxnl1), encodes the Q8VC33 UniProt protein, which has limited similarity to the thioredoxin superfamily and which exerts trophic activity on cone photoreceptors (LEVEILLARD et al., Nat. Genet. vol. 36(7), p:755-759, 2004).

However there is an existing need to identify trophic factors of neurons, in particular cone photoreceptors that will strengthen the treatment and diagnosis of degenerative disorders, in particular retinal degenerative disorders.

SUMMARY OF THE INVENTION

The inventors have now identified a new isoform of the RdCVF2 polypeptide (named "RdCVF2v") described in the International patent application WO02081513.

The present invention relates to a polypeptide comprising:
a) the amino acid sequence as set forth in SEQ ID NO:1 or a variant thereof, wherein said variant has at least 90% identity with SEQ ID NO:1 and
b) the amino acid sequence as set forth in SEQ ID NO:2 or a variant thereof, wherein said variant has at least 90% identity with SEQ ID NO:2 and
c) the amino acid sequence as set forth in SEQ ID NO:3 or a variant thereof, wherein said variant has at least 90% identity with SEQ ID NO:3
or a fragment thereof wherein said fragment thereof comprises the amino acid sequence as set forth in SEQ ID NO:2 or a variant thereof having at least 90% identity with SEQ ID NO:2 and wherein said fragment thereof exhibits neuron rescue activity.

The present invention also relates to an isolated nucleic acid molecule encoding said polypeptide or fragment thereof.

The present invention also relates to the treatment of a neurodegenerative disorder.

DETAILED DESCRIPTION OF THE INVENTION

Definitions

As used herein, the term "RdCVF2" refers to any isoform of Rod-derived Cone Viability Factor 2.

As used herein, the term "RdCVF2v" refers to a polypeptide consisting of the amino acid sequence as set forth in SEQ ID NO:4.

(MVDVLGGRRLVTREGTVVEAEVALQNKVVALYFAAGRCSPSRDFTPLL

CDFYTELVSEARRPAPFEVVFVSADGSAEEMLDFMRELHGSWLALPFHD

PYRQSQCGPIPPNLGFSIHGAPVCQRFLPFTIGVSGIHMSQEPQDCELK

KRYEITAIPKLVVIKQNGAVITNKGRKQIRERGLACFQNWVEAADVFQN

FSG).

SEQ ID NO:4 consists in the following sequences, from the N-terminus to the C-terminus:
the amino acid sequence which is common to both the long and short isoforms of RdCVF2 as described in WO 02081513:

(SEQ ID NO :1)
MVDVLGGRRLVTREGTVVEAEVALQNKVVALYFAAGRCSPSRDFTPL

LCDFYTELVSEARRPAPFEVVFVSADGSAEEMLDFMRELHGSWLALP

FHDPYR;

an amino acid sequence which is unique to this variant isoform:

(SEQ ID NO :2)
QSQCGPIPPNLGFSIHGAPVCQRFLPFTIGVSGIHMSQEPQDC the amino acid sequence which is present is the long isoform but not the short isoform of RdCVF2:

(SEQ ID NO :3)
ELKKRYEITAIPKLVVIKQNGAVITNKGRKQIRERGLACFQNWVEAADV

FQNFSG.

As used herein, the term "polypeptide of the invention" refers to a polypeptide comprising:
  a) the amino acid sequence as set forth in SEQ ID NO:1 or a variant thereof, wherein said variant has at least 90% identity with SEQ ID NO:1 and
  b) the amino acid sequence as set forth in SEQ ID NO:2 or a variant thereof, wherein said variant has at least 90% identity with SEQ ID NO:2 and
  c) the amino acid sequence as set forth in SEQ ID NO:3 or a variant thereof, wherein said variant has at least 90% identity with SEQ ID NO:3
  or a fragment thereof wherein said fragment thereof comprises the amino acid sequence as set forth in SEQ ID NO:2 or a variant thereof having at least 90% identity with SEQ ID NO:2 and wherein said fragment thereof exhibits neuron rescue activity.

As used herein, the expression "compound which selectively binds to a polypeptide of the invention" refers to a compound, such as an antibody or an aptamer, which binds to a polypeptide of the invention but not to the other isoforms of RdCVF. In other terms, a compound which selectively binds to a polypeptide of the invention binds, at least in part, to the amino acid sequence as set forth in SEQ ID NO:2 or variant thereof.

As used herein, the terms "nucleic acid molecule of the invention" refers to a nucleic acid molecule encoding a polypeptide of the invention.

As used herein, the terms "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. In one, non-limiting example stringent hybridization conditions are hybridization at 6× sodium chloride/sodium citrate (SSC) at about 45° C., followed by one or more washes in 0.1×SSC, 0.2% SDS at about 68° C. A preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). Preferably, an isolated nucleic acid molecule of the invention that hybridizes under stringent conditions to the sequence of SEQ ID NO:5, or a complement thereof, corresponds to a naturally-occurring nucleic acid molecule.

The expression "nucleic acid molecule which selectively hybridizes to a nucleic acid molecule encoding SEQ ID NO:2" refers to a nucleic acid which hybridizes under stringent conditions to a nucleic acid containing a nucleic acid sequence encoding SEQ ID NO:2 or a variant thereof having at least 90%, preferably 91%, 92%, 93%, 94%, 95%, 96%, 97%, 98%, 99%, or 99.5% identity with SEQ ID NO:2.

As used herein, a "naturally-occurring" nucleic acid molecule refers to a RNA or DNA molecule having a nucleotide sequence that occurs in nature (e.g., encodes a natural protein).

By "purified" and "isolated" it is meant, when referring to a polypeptide or a nucleotide sequence, that the indicated molecule is present in the substantial absence of other biological macromolecules of the same type. The term "purified" as used herein preferably means at least 75% by weight, more preferably at least 85% by weight, still preferably at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

Two amino acid sequences or nucleic acid sequences are "substantially homologous" or "substantially similar" when greater than 85%, preferably greater than 90% of the amino acids or nucleic acid sequences are identical, or greater than about 90%, preferably greater than 95%, are similar (functionally identical). To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences. In one embodiment, the two sequences are the same length. The determination of percent identity between two sequences can be accomplished using a mathematical algorithm. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The terms "antibody" and "immunoglobulin" have the same meaning and are used indifferently in the present invention. Antibody refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (λ) and kappa (K). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding affinity and specificity of the natural Fv region of a native immunoglobulin binding-site. The light and heavy chains of an immunoglobulin each have three CDRs, designated L-CDR1, L-CDR2, L-CDR3 and H-CDR1, H-CDR2, H-CDR3, respectively. Therefore, an antigen-binding site includes six CDRs, comprising the CDR set from each of a heavy and a light chain V region. Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al (Sequences of Proteins of Immunological Interest (National Institutes of Health, Bethesda, Md., 1991). As used herein, a "human framework region" is a framework region that is substantially identical (about 85%, or more, in particular 90%, 95%, or 100%) to the framework region of a naturally occurring human antibody.

The term "monoclonal antibody" or "mAb" as used herein refers to an antibody molecule of a single amino acid composition, that is directed against a specific antigen and that is produced by a single clone of B cells or hybridoma.

The term "chimeric antibody" refers to an engineered antibody which comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

"Antibody fragments" comprise a portion of an intact antibody, preferably the antigen binding or variable region of the intact antibody. Examples of antibody fragments include Fv, Fab, F(ab')2, Fab', dsFv, scFv, sc(Fv)2, diabodies and multispecific antibodies formed from antibody fragments.

As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

The term "neuron" refers to an electrically excitable cell in the nervous system that can process and transmit information. Typically a neuron according to the invention is a vertebrate neuron, preferably a mammal neuron, even more preferably a human neuron. The term neuron includes but is not limited to brain neurons (e.g. bipolar—pseudounipolar—multipolar—pyramidal—Purkinje—granule—cortical . . . ), photoreceptors, and olfactory sensitive neurons.

The expression "neuron rescue activity" refers to the ability of the polypeptides of the invention to maintain the survival of a neuron. Typically, for assessing the ability to exhibit neuron rescue activity of a polypeptide, the skilled person may incubate neurons (eg Purkinje cells, cortical neurons, photoreceptors, olfactory sensitive neurons . . . ) with conditioned medium from cells expressing the polypeptide to be assessed and subsequently, the number of surviving neurons is evaluated. Typically, a polypeptide is deemed to exhibit neuron rescue activity if it increases the number of viable neurons in at least one of the following assays, described in the Example below: cone rescue activity, olfactory sensitive neuron rescue activity, Purkinje cell rescue activity and cortical neuron rescue activity.

In the context of the invention, the term "treating" or "treatment", as used herein, means reversing, alleviating, inhibiting the progress of, or preventing the disorder or condition to which such term applies, or one or more symptoms of such disorder or condition (e.g., neurodegenerative disorders).

As used herein, the expression "neurodegenerative disorder" refers to a disease associated with the degeneration of neurons such as degenerative disorders of the central nervous system, retinal degenerative disorders, or degenerative disorders of the olfactory neurons. Typically, neurodegenerative disorders according to the invention include, but are not limited to, alcoholism, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Progressive Supranuclear Palsy, Refsum's disease, Sandhoff's disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and retinal degenerative disorders, The term "retinal degenerative disorders" encompasses all diseases associated with cone degeneration. Retinal degenerative disorders include but are not limited to Retinitis Pigmentosa, age-related macular degeneration, Bardet-Biedel syndrome, Bassen-Kornzweig syndrome, Best disease, choroidema, gyrate atrophy, Leber congenital amaurosis, Refsum disease, Stargardt disease or Usher syndrome.

According to the invention, the term "patient" or "patient in need thereof" is intended for a human or non-human mammal affected or likely to be affected with retinal degenerative disorders.

The term "biological sample" means any biological sample derived from a patient. Examples of such samples include fluids, tissues, cell samples, organs, biopsies, etc. Preferred biological samples are whole blood, serum, or plasma.

Polypeptides of the Invention

One aspect of the invention pertains to a polypeptide comprising:
a) the amino acid sequence as set forth in SEQ ID NO:1 or a variant thereof, wherein said variant has at least 90% identity with SEQ ID NO:1 and
b) the amino acid sequence as set forth in SEQ ID NO:2 or a variant thereof, wherein said variant has at least 90% identity with SEQ ID NO:2 and
c) the amino acid sequence as set forth in SEQ ID NO:3 or a variant thereof, wherein said variant has at least 90% identity with SEQ ID NO:3
or a fragment thereof wherein said fragment thereof comprises the amino acid sequence as set forth in SEQ ID NO:2 or a variant thereof having at least 90% identity with SEQ ID NO:2 and wherein said fragment thereof exhibits neuron rescue activity.

In one embodiment the polypeptide of the invention comprises the amino acid sequence as set forth in SEQ ID NO:1 or a variant thereof, wherein said variant has at least 91%, preferably 92%, 93%, 94%, 95%, 96%, 97%, 98%, 99%, or 99.5% identity with SEQ ID NO:1.

In one embodiment the polypeptide of the invention comprises the amino acid sequence as set forth in SEQ ID NO:2 or a variant thereof, wherein said variant has at least 91%, preferably 92%, 93%, 94%, 95%, 96%, 97%, 98%, 99%, or 99.5% identity with SEQ ID NO:2.

In one embodiment the polypeptide of the invention comprises the amino acid sequence as set forth in SEQ ID NO:2 or a variant thereof, wherein said variant has at least 91%, preferably 92%, 93%, 94%, 95%, 96%, 97%, 98%, 99%, or 99.5% identity with SEQ ID NO:2.

In one embodiment the polypeptide of the invention comprises variants of SEQ ID NO:1, SEQ ID NO:2 and SEQ ID NO:3 wherein said variants have at least 91%, preferably, 92%, 93%, 94%, 95%, 96%, 97%, 98%; 99%, 99.5% identity with SEQ ID NO:1, SEQ ID NO:2 and SEQ ID NO:3 respectively, each value being selected independently.

According to one aspect of the invention, the polypeptide of the invention has a length which does not exceed 500 amino acids, preferably, 400 amino acids, preferably 350, 300, 290, 280, 270, 260, 250, 240, 230, 220, 210, 20, 198 amino acids.

According to one aspect of the invention, the polypeptide of the invention has a length which does not exceed 150, preferably 145, even more preferably 143 amino acids.

The polypeptides of the invention encompass polypeptides comprising amino acid sequences as set forth in SEQ ID NO: 1, SEQ ID NO:2 and SEQ ID NO:3 or variants thereof in any order. In a preferred embodiment, the invention relates to a polypeptide or fragment thereof as described above, wherein said amino acid sequence as set forth in SEQ ID NO:1 or variant thereof is located at the N-terminus of the amino acid sequence as set forth in SEQ ID NO: 2 or variant thereof and wherein said amino acid sequence as set forth in SEQ ID NO:2 or variant thereof is located at the N-terminus of the amino acid sequence as set forth in SEQ ID NO: 3 or variant thereof.

In a particular embodiment, the invention relates to a polypeptide or fragment thereof as described above wherein said polypeptide or fragment thereof has at least 90% identity, preferably at least 91%, 92%, 93%, 94%, 95%, 96%, 97%, 98%, 99%, or 99.5% identity, with the amino acid sequence as set forth in SEQ ID NO:4 and wherein said polypeptide or fragment thereof comprises an amino acid sequence having at least 90% identity, preferably at least 91%, 92%, 93%, 94%, 95%, 96%, 97%, 98%, 99%, or 99.5% identity with SEQ ID NO:2.

Typically the polypeptide of the invention may consist of the amino acid sequence of SEQ ID NO:4 (RdCVF2v).

Typically, the polypeptides of the invention exhibit neuron rescue activity.

In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

The invention also provides chimeric or fusion proteins. One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

Typically variants according to the invention can be generated by mutagenesis, e.g., discrete point mutation or truncation.

The polypeptides of the invention can exhibit post-translational modifications, including, but not limited to glycosylations, (e.g., N-linked or O-linked glycosylations), myristylations, palmitylations, acetylations and phosphorylations (e.g., serine/threonine or tyrosine).

The polypeptides of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired polypeptide into expression vectors and introduction of such vectors into suitable eukaryotic or prokaryotic hosts that will express the desired polypeptide, from which they can be later isolated using well-known techniques.

Polypeptides of the invention can be use in an isolated (e.g., purified) form or contained in a vector, such as a membrane or lipid vesicle (e.g. a liposome).

Nucleic Acid Molecules of the Invention

One aspect of the invention pertains to isolated nucleic acid molecules that encode a polypeptide of the invention, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules.

The invention also relates to an isolated nucleic acid molecule encoding a polypeptide of the invention.

In particular embodiment, the invention relates to an isolated nucleic acid molecule having the nucleotide sequence as set forth in SEQ ID NO:5.

A nucleic acid molecule of the present invention can be isolated using standard molecular biology techniques and the sequence information provided herein. Using all or a portion of the nucleic acid sequences of the invention as a hybridization probe, nucleic acid molecules of the invention can be isolated using standard hybridization and cloning techniques (e.g., as described in Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:5. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide.

In one embodiment, the oligonucleotide comprises a region of nucleotide sequence that hybridizes under stringent conditions to at least about 12, preferably about 25, more preferably about 50 consecutive nucleotides of the sense or anti-sense sequence of SEQ ID NO:5.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which express or not the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ from the nucleotide sequence of SEQ ID NO:5 due to degeneracy of the genetic code and thus encode the same protein as that encoded by the nucleotide sequence of SEQ ID NO:5.

In addition to the nucleotide sequences of SEQ ID NO:5, it will be appreciated by those skilled in the art that DNA sequence polymorphisms that lead to changes in the amino acid sequence may exist within a population. Such genetic polymorphisms may exist among individuals within a population due to natural allelic variation. An allele is one of a group of genes which occur alternatively at a given genetic locus. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In one embodiment, polymorphisms that are associated with a retinal degenerative disorder are used as markers to diagnose said disease or disorder.

Moreover, nucleic acid molecules encoding proteins of the invention from other species (homologues), which have a nucleotide sequence which differs from that of rat protein described herein are intended to be within the scope of the invention.

Nucleic acid molecules corresponding to natural allelic variants and homologues of a cDNA of the invention can be isolated based on their identity to the human nucleic acid molecule disclosed herein using the human cDNAs, or a portion thereof, as a hybridization probe according to standard hybridization techniques under stringent hybridization conditions.

Accordingly, in another embodiment, an isolated nucleic acid molecule of the invention is at least 100, 200, 300, 400, or 500 contiguous nucleotides in length and hybridizes under stringent conditions to the nucleic acid molecule comprising the nucleotide sequence, preferably the coding sequence, of SEQ ID NO:5 or a complement thereof.

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., mouse and human) may be essential for activity and thus would not be likely targets for alteration.

Mutations can be introduced by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

Following mutagenesis, the encoded protein can be expressed recombinantly and the activity of the protein can be determined.

In a preferred embodiment, a mutant polypeptide that is a variant of the invention can be assayed for its ability to exhibit neuron rescue activity.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g, phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Recombinant Expression Vectors and Host Cells

Another aspect of the invention pertains to vectors, preferably expression vectors, containing a nucleic acid encoding a polypeptide of the invention (or a portion thereof).

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., E. coli) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301-315) and pET 11d (Studier et al., Gene Expression Technology Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET Id vector relies on transcription from a T7 gn10-lac fusion promoter mediated by a coexpressed viral RNA polymerase (T7 gn1). This viral polymerase is supplied by host strains BL21(DE3) or HMS174(DE3) from a resident) prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerivisae include pYepSec1 (Baldari et al. (1987) EMBO J. 6:229-234), pMFa (Kurjan and Herskowitz, (1982) Cell 30:933-943), pJRY88 (Schultz et al. (1987) Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Neuron-specific regulatory elements are known in the art (e.g., the neurofilament promoter; Byrne and Ruddle (1989) Proc. Natl. Acad. Sci. USA 86:5473-5477).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews-Trends in Genetics, Vol. 1(1) 1986).

Another aspect of the invention pertains to host cells into which a recombinant expression vector of the invention has been introduced.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous gene within a cell, cell line or microorganism may be modified by inserting a DNA regulatory element heterologous to the endogenous gene of interest into the genome of a cell, stable cell line or cloned microorganism such that the inserted regulatory element is operatively linked with the endogenous gene and controls, modulates or activates. For example, endogenous genes which are normally "transcriptionally silent", i.e., genes which are normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous genes may be activated by insertion of a promiscuous regulatory element that works across cell types.

A heterologous regulatory element may be inserted into a stable cell line or cloned microorganism, such that it is operatively linked with and activates expression of endogenous genes, using techniques, such as targeted homologous recombination, which are well known to those of skill in the art, and described e.g., in Chappel, U.S. Pat. No. 5,272,071; PCT publication No. WO 91/06667, published May 16, 1991.

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The present invention also relates to a method for producing a recombinant host cell expressing an polypeptide according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said polypeptide. Such recombinant host cells can be used for the production of polypeptides according to the present invention, as previously described.

The invention further relates to a method of producing a polypeptide according to the invention, which method comprises the steps consisting of: (i) culturing a transformed host cell according to the invention under conditions suitable to allow expression of said polypeptide; and (ii) recovering the expressed polypeptide.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity.

As used herein, a "transgenic animal" is a non-human animal, preferably a mammal, more preferably a rodent such as a rat or mouse, in which one or more of the cells of the animal includes a transgene.

Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal.

As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Biotechnology 2:823-829 and in PCT Publication Nos. WO 90/11354, WO 91/01140, WO 92/0968 and WO 93/04169.

In another embodiment, transgenic non-human animals can be produced which contain selected systems which allow for regulated expression of the transgene. One example of such a system is the cre/toxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of Saccharomyces cerevisiae (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication NOS. WO 97/07668 and WO 97/07669.

Another object of the invention relates is compounds which selectively bind to a polypeptide of the invention. Such compounds are particularly useful in carrying out the methods of the invention. Examples of compounds which selectively bind to a polypeptide of the invention are antibodies and aptamers.

Antibodies of the Invention

Accordingly, in one aspect, the invention provides substantially purified antibodies or fragment thereof, and non-human antibodies or fragments thereof, which antibodies or fragments specifically bind to a polypeptide of the invention.

In various embodiments, the substantially purified antibodies of the invention, or fragments thereof, can be human, non-human, chimeric and/or humanized antibodies. Such non-human antibodies can be goat, mouse, sheep, horse, chicken, rabbit, or rat antibodies. In addition, the antibodies of the invention can be polyclonal antibodies or monoclonal antibodies.

In still a further aspect, the invention provides monoclonal antibodies or fragments thereof. The monoclonal antibodies can be human, humanized, chimeric and/or non-human antibodies.

Antibodies according to invention may be produced by any technique known in the art, such as, without limitation, any chemical, biological, genetic or enzymatic technique, either alone or in combination.

Polyclonal antibodies can be prepared by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77-96) or trioma techniques. The technology for producing hybridomas is well known (see generally Current Protocols in Immunology (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

Completely human antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. No. 5,625,126; U.S. Pat. Nos. 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

The present invention encompasses antibody fragments of the antibodies of the invention. Examples of antibody fragments include Fv, Fab, F(ab')2, Fab', dsFv, scFv, sc(Fv)$_2$, diabodies and multispecific antibodies formed from antibody fragments.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques. "dsFv" is a VH::VL heterodimer stabilised by a disulphide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Aptamers of the Invention

In another embodiment, the invention relates to an aptamer directed against a polypeptide of the invention.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as E. coli Thioredoxin A, that are selected from combinatorial libraries by two hybrid methods (Colas et al., 1996).

Screening Methods

The invention provides a method (also referred to herein as a "screening method") for identifying modulators, i.e., candidate or test compounds or agents (e.g., peptides, peptidomimetics, small molecules or other drugs) which bind to polypeptide of the invention or have a stimulatory on, for example, expression or activity of a polypeptide of the invention.

In one embodiment, the invention provides assays for screening candidate or test compounds that increase the activity of a polypeptide of the invention or biologically active portion thereof. More particularly, the invention provides assays for screening candidates or test compounds that can stimulate the expression of the polypeptides of the invention.

The candidate or test compounds may be assayed for their ability to stimulate the expression of the polypeptides of the invention. For example, a reporting system assay may be used to measure the expression of the polypeptide of the invention. A host cell of the invention may be used in that purpose. In a particularly embodiment the vector may encode for a fusion protein comprising a polypeptide of the invention and a fluorescent protein. Naturally fluorescent, bioluminescent or phosphorescent proteins include GFP derived from Aequorea Victoria, and a growing number of sequence variants of GFP with useful properties. The list also includes the red fluorescent protein (RFP) derived from Discosoma; and the kindling fluorescent protein (KFP1) derived from Anemonia. These proteins are autocatalytic enzymes that are all capable of generating highly visible, efficiently emitting internal fluorophores as a result of endo-cyclization of core amino acid residues. Another common feature of the fluorescent proteins is that the signal is stable, species independent, and does not require any substrates or cofactors for the generation of a signal. Direct detection of fluorescence by visual observation (e.g., under broad spectrum UV light) may be the used to quantify the amount of the fusion protein produced under the presence or absence of the candidate or test compounds.

The candidate or test compounds can be then assayed for their ability to inhibit cone photoreceptor degeneration. Any suitable assay known to one of skill in the art can be used to monitor such effects (such as the one described in Example).

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds.

Diagnostic Methods of the Invention

The present invention also pertains to diagnostic assays, prognostic assays, and monitoring assays.

Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention (e.g. neurodegenerative disorders).

The invention also provides for prognostic (or predictive) assays for determining whether an individual is at risk of developing a disorder associated with aberrant expression or activity of a polypeptide of the invention (e.g. neurodegenerative disorders). For example, mutations in a nucleic acid molecule of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Yet another aspect of the invention pertains to monitoring the influence of agents (e.g., drugs or other compounds) on the expression or activity of a polypeptide of the invention, in clinical trials or treatments.

The invention relates to a method for detecting the presence of a polypeptide of the invention in a sample, comprising the steps of:
  a) contacting the sample with a compound which selectively binds to a polypeptide of the invention; and
  b) determining whether the compound binds to said polypeptide in the sample.

The invention also relates to a method for detecting the presence of a nucleic acid molecule of the invention in a sample, comprising the steps of:
  a) contacting the sample with a nucleic acid probe or primer which selectively hybridizes to a nucleic acid molecule encoding SEQ ID NO:2; and
  b) determining whether the nucleic acid probe or primer binds to said nucleic acid molecule in the sample.

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labelled nucleic acid probe capable of hybridizing to mRNA or genomic DNA encoding a polypeptide of the invention. The nucleic acid probe can be, for example, the nucleic acid of SEQ ID NO:2. or a portion thereof, such as an oligonucleotide of at least 15, 30, or 50 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies may be prepared according to the methods as above describes.

The term "labelled", with regard to the probe or antibody, is intended to encompass direct labelling of the probe or antibody by coupling (i.e., physically linking) a detectable substance to the probe or antibody, as well as indirect labelling of the probe or antibody by reactivity with another reagent that is directly labelled. Examples of indirect labelling include detection of a primary antibody using a fluorescently labelled secondary antibody and end-labelling of a DNA probe with biotin such that it can be detected with fluorescently labelled streptavidin.

The detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labelled antibody directed against the polypeptide. For example, the antibody can be labelled with a radioactive marker whose presence and location in a subject can be detected by standard imaging techniques.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample. Such kits can be used to determine if a subject is suffering from or is at increased risk of developing a disorder associated with aberrant expression of a polypeptide of the invention (e.g. retinal degenerative disorders). The kit, for example, can comprise a labelled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

The kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

The kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

The methods described herein can furthermore be utilized as diagnostic or prognostic assays to identify subjects having or at risk of developing a disease or disorder associated with aberrant expression or activity of a polypeptide of the invention (e.g. retinal degenerative disorders). For example, the assays described herein, such as the preceding diagnostic assays or the following assays, can be utilized to identify a subject having or at risk of developing a disorder associated with aberrant expression or activity of a polypeptide of the invention. Alternatively, the prognostic assays can be utilized to identify a subject having or at risk for developing such a disease or disorder.

Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, polypeptide, nucleic acid, small molecule, or other drug candidate) to treat a disease or disorder associated with aberrant expression or activity of a polypeptide of the invention (e.g. retinal degenerative disorders). For example, such methods can be used to determine whether a subject can be effectively treated with a specific agent or class of agents (e.g., agents of a type which increase the activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the absence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention (e.g. retinal degenerative disorders). In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention.

For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a gene (see, e.g., Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127-162; and Griffin et al. (1993) Appl. Biochem. Biotechnol. 38:147-159).

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) Proc. Natl. Acad. Sci. USA 86:2766; see also Cotton (1993) Mutat. Res. 285:125-144; Hayashi (1992) Genet.

Anal. Tech. Appl. 9:73-79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to insure that it does not completely denature, for example by adding a 'GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6: 1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention.

The invention will be further illustrated by the following figures and examples. However, these examples and figures should not be interpreted in any way as limiting the scope of the present invention.

Therapeutic Methods and Pharmaceutical Compositions

The polypeptides, nucleic acid molecules, vectors, host cells of the invention may be particularly suitable for therapeutic purposes. For example, polypeptides, nucleic acid molecules, vectors, host cells of the invention may be suitable for the treatment of a neurodegenerative disorder.

As an example of neurodegenerative disorders of the central nervous system, one can cite Alzheimer's Disease, Parkinson's Disease, and Huntington's Disease/Chorea.

In particular embodiment, the neurodegenerative disorder is a retinal degenerative disorder. Typically said retinal degenerative disorder is selected from the group consisting of Retinitis Pigmentosa, age-related macular degeneration, Bardet-Biedel syndrome, Bassen-Kornzweig syndrome, Best disease, choroidema, gyrate atrophy, Leber congenital amaurosis, Refsum disease, Stargardt disease or Usher syndrome. In a preferred embodiment said degenerative disease is Retinitis Pigmentosa.

In one embodiment, the invention provides a method for treating neurodegenerative disorders comprising administering a patient in need thereof with a therapeutically effective amount of a polypeptide or nucleic acid molecule of the invention.

By a "therapeutically effective amount" of the polypeptide or nucleic acid molecule of the invention is meant a sufficient amount of the nucleic acid molecule or polypeptide to treat neurodegenerative disorders at a reasonable benefit/risk ratio applicable to any medical treatment. It will be understood, however, that the total daily usage of the polypeptides or nucleic acid molecules and compositions of the present invention will be decided by the attending physician within the scope of sound medical judgment. The specific therapeutically effective dose level for any particular patient will depend upon a variety of factors including the disorder being treated and the severity of the disorder; activity of the specific polypeptide employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

The polypeptides, nucleic acid molecules, vectors or host cells of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the polypeptide or nucleic acid molecule of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A polypeptide of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptide may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the polypeptides formulated for parenteral administration, such as intravenous or intramuscular injection, other pharmaceutically acceptable forms include, e.g. tablets or other solids for oral administration; liposomal formulations; time release capsules; and any other form currently used.

A polypeptide, nucleic acid molecule or a vector of the invention can be delivered in a pharmaceutically acceptable ophthalmic vehicle, such that the polypeptide can penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, a polypeptide, nucleic acid molecule or a vector of the invention may be injected directly into the vitreous, aqueous humour, ciliary body tissue(s) or cells and/or extra-ocular muscles by electroporation means.

A polypeptide, nucleic acid molecule or a vector of the invention may also be combined with other compounds known to exert neuron trophic activities. For example, the polypeptides of the invention may be combined with the Rod-derived Cone Viability Factor (RdCVF) for the treatment of neurodegenerative disorders, especially retinal degenerative disorders (e.g. Retinitis Pigmentosa). The RdCVF1 and RdCVF2 polypeptides and genes have been described in the International Patent Applications published under numbers WO02081513 and WO2005/113586 and in LEVEILLARD et al., Nat. Genet. vol. 36(7), p:755-759, 2004) and in Channel et al., BMC Molecular Biology, 2007, 8:74. Accordingly, the present invention also relates to pharmaceutical compositions comprising a first compound selected from the group consisting of the polypeptides or nucleic acid molecules of the invention and a second compound selected from the group consisting of a nucleic acid sequence encoding for RdCVF1 or RdCVF2, and RdCVF1 or RdCVF2 themselves.

Typically, the present invention also relates to a composition for the treatment of a neurodegenerative disorder comprising:
a) a polypeptide of the invention or an isolated nucleic acid encoding a polypeptide of the invention, and
b) a Rod-derived Cone viability factor (e.g. RdCVF1 or RdCVF2).

The present invention also relates to a kit for the treatment of a neurodegenerative disorder comprising:
a) a polypeptide of the invention or an isolated nucleic acid encoding a polypeptide of the invention and
b) a Rod-derived Cone viability factor (e.g. RdCVF1 or RdCVF2).

Typically, the 2 components of the kit may be separately administered to the patient.

EXAMPLE

The novel isoform RdCVF2v was identified by large scale sequencing of a normalized retinal mouse cDNA library. This isoform was very rare in comparison to the known isoforms of RdCVF2.

Neuron Rescue Activity

RdCVF2v is tested in vitro for its neuron rescue activity, i.e. its ability to prevent the death of neurons in primary cultures.

Briefly, an expression vector encoding RdCVF2v is transfected into a plurality of cells (COS-1 cells). 48 hours after transfection, the conditioned medium from the transfected cells is harvested and incubated with primary culture of neurons (photoreceptors, olfactory sensitive neurons, . . . ). After a period of culture, neurons are fixed and labelled, and counted.

1) Cone Rescue Activity

The primary culture is a cone-enriched primary cell culture system from chicken embryo (60-80% of cones) as described in Fintz et al. (Invest. Ophtamol. Vis. Sci, vol 44(2): 818-825, 2003.)

After 7 days of incubation, a period over which these post-mitotic cells degenerate, the viability of the cells in the culture was scored using the Live/Dead assay (Molecular Probes) and a cell counting platform as previously described (Leveillard et al., 2004).

The trophic activity of RdCVF2v (polypeptide of the invention) was compared with that of other trophic factors:

| | Factor added | | | |
|---|---|---|---|---|
| | None (control) | RdCVF | RdCVF2v | RdCVF2 |
| Number of live cells | 70 | 133 | 146 | 122 |

The polypeptide of the invention presents a trophic activity which is greater than that of RdCVF and RdCVF2.

2) Olfactory Sensitive Neuron Rescue Activity

Adult mice are killed by decapitation. The posterior part of the nasal septum is dissected free of the nasal cavity and immediately placed in ice-cold DMEM containing 50 µg/ml gentamicin (Eurobio; Gibco) and 10 (v/v) fetal calf serum (eurobio). The cartilage of the septum is removed and the olfactory mucosa is incubated for 30 min at 37° C. in a 2.4 U/MI dispase II solution (Roche. The olfactory epithelium is carefully separated from the underlying lamina propria under the dissection microscope and gently triturated about 20 times to separate the cells. The resulting cell suspension is transferred to a 50 ml conical tube and the dispase is inactivated by adding 40 ml of HBSS without calcium and magnesium. The cell suspension is centrifuged at 700 rpm for 5 min, and the pellet containing the cells is resuspended in a medium composed of DMEM containing insulin (10 µg/ml, Sigma), transferin (10 µg/ml, Sigma), selenium (10 µg/ml, Sigma), calf foetal serum (5%), ascorbic acid (200 µM). Cells are plated on 12 mm sterile glass coverslips coated with 5 µg/cm$^2$ human collagen IV (Sigma); thus providing a primary culture of Olfactory Sensitive Neurons (OSN).

After 4 days of culture with or without RdCVF2v, cells are fixed and labelled with tubulin III, and counted.

3) Purkinje Cell Rescue Activity

After decapitation of mouse at postnatal day 1-3, brains are dissected out into cold Grey's balanced salt solution containing 5 mg/ml glucose, and the meninges are removed. Cerebellar parasagittal slices (35° or 250 µm thick) are cut on a McIlwain tissue chopper and transferred onto membrane of 30 mm Millipore culture inserts with 0.4 µm pore size (Millicel; Millipore, Bedford, Mass.). Slices are maintained in culture in 6-well plates containing 3 ml of medium at 35° in an atmosphere of humidified 5% $CO_2$. The medium is composed of 50% basal medium with Earle's salts (Invitrogen), 25% HBSS (Invitrogen), 25% horse serum (Invitrogen), L-glutamine (1 mM) and 5 mg/ml glucose (Stoppini et al., J Neurosci Methods, vol 37(2), p 173-82, 1991).

After 4 days of culture with or without RdCVF2v, cells are fixed and labelled with tubulin III, and counted.

4) Cortical Neuron Rescue Activity

Serum-free preparation of mouse cortical primary cultures is performed with mouse at postnatal day 1. After removal of the meninges, entire cortices are mechanically dissociated un a phosphate buffer saline glucose solution without added divalent cations (100 mM NaCl, 3 mM KCl, 1.5 mM KH2PO4, 7.9 mM Na2HPO4, 33 mM glucose, 100 U/ml penicillin and 100 µg/ml streptomycin) and resuspended in Neurobasal medium (Invitrogen) containing 2% B27 supplement (Gibco), 0.5 mM glutamine; and 25 µM glutamate. Cells are then cultured onto poly-ornithine coated coverslips to produce cultures highly enriched in cortical neurons.

After 4 days of culture with or without RdCVF2v, cells are fixed and labelled with tubulin III, and counted.

Animal Models of Neurodegeration

The activity of RdCVF2v is tested in vivo on animal models (rd1 mouse, P23H transgenic rat, . . . ) of neurodegeneration after adeno-associated viral RdCVF2v delivery.

The invention claimed is:

1. An isolated polypeptide comprising the amino acid sequence as set forth in SEQ ID NO:4.

2. The polypeptide according to claim 1 wherein said polypeptide has a length of no more than 250 amino acids.

3. The polypeptide according to claim 1 which consists of the amino acid sequence of SEQ ID NO:4.

4. The polypeptide according to claim 1 wherein said polypeptide exhibits neuronal rescue activity.

5. The polypeptide according to claim 2 wherein said polypeptide exhibits neuronal rescue activity.

* * * * *

SEQUENCE LISTING

<160> NUMBER OF SEQ ID NOS: 5

<210> SEQ ID NO 1
<211> LENGTH: 100
<212> TYPE: PRT
<213> ORGANISM: Mus musculus

<400> SEQUENCE: 1

Met Val Asp Val Leu Gly Gly Arg Arg Leu Val Thr Arg Glu Gly Thr
1               5                   10                  15

Val Val Glu Ala Glu Val Ala Leu Gln Asn Lys Val Val Ala Leu Tyr
            20                  25                  30

Phe Ala Ala Gly Arg Cys Ser Pro Ser Arg Asp Phe Thr Pro Leu Leu
        35                  40                  45

Cys Asp Phe Tyr Thr Glu Leu Val Ser Glu Ala Arg Arg Pro Ala Pro
    50                  55                  60

Phe Glu Val Val Phe Val Ser Ala Asp Gly Ser Ala Glu Glu Met Leu
65                  70                  75                  80

Asp Phe Met Arg Glu Leu His Gly Ser Trp Leu Ala Leu Pro Phe His
                85                  90                  95

Asp Pro Tyr Arg
            100

<210> SEQ ID NO 2
<211> LENGTH: 43
<212> TYPE: PRT
<213> ORGANISM: Mus musculus

<400> SEQUENCE: 2

Gln Ser Gln Cys Gly Pro Ile Pro Pro Asn Leu Gly Phe Ser Ile His
1               5                   10                  15

Gly Ala Pro Val Cys Gln Arg Phe Leu Pro Phe Thr Ile Gly Val Ser
            20                  25                  30

Gly Ile His Met Ser Gln Glu Pro Gln Asp Cys
        35                  40

<210> SEQ ID NO 3
<211> LENGTH: 55
<212> TYPE: PRT
<213> ORGANISM: Mus musculus

<400> SEQUENCE: 3

Glu Leu Lys Lys Arg Tyr Glu Ile Thr Ala Ile Pro Lys Leu Val Val
1               5                   10                  15

Ile Lys Gln Asn Gly Ala Val Ile Thr Asn Lys Gly Arg Lys Gln Ile
            20                  25                  30

Arg Glu Arg Gly Leu Ala Cys Phe Gln Asn Trp Val Glu Ala Ala Asp
        35                  40                  45

Val Phe Gln Asn Phe Ser Gly
    50                  55

<210> SEQ ID NO 4
<211> LENGTH: 198
<212> TYPE: PRT
<213> ORGANISM: Mus musculus

<400> SEQUENCE: 4

Met Val Asp Val Leu Gly Gly Arg Arg Leu Val Thr Arg Glu Gly Thr
1               5                   10                  15

```
Val Val Glu Ala Glu Val Ala Leu Gln Asn Lys Val Val Ala Leu Tyr
            20                  25                  30

Phe Ala Ala Gly Arg Cys Ser Pro Ser Arg Asp Phe Thr Pro Leu Leu
            35                  40                  45

Cys Asp Phe Tyr Thr Glu Leu Val Ser Glu Ala Arg Arg Pro Ala Pro
            50                  55                  60

Phe Glu Val Val Phe Val Ser Ala Asp Gly Ser Ala Glu Glu Met Leu
65                  70                  75                  80

Asp Phe Met Arg Glu Leu His Gly Ser Trp Leu Ala Leu Pro Phe His
                85                  90                  95

Asp Pro Tyr Arg Gln Ser Gln Cys Gly Pro Ile Pro Pro Asn Leu Gly
                100                 105                 110

Phe Ser Ile His Gly Ala Pro Val Cys Gln Arg Phe Leu Pro Phe Thr
            115                 120                 125

Ile Gly Val Ser Gly Ile His Met Ser Gln Glu Pro Gln Asp Cys Glu
            130                 135                 140

Leu Lys Lys Arg Tyr Glu Ile Thr Ala Ile Pro Lys Leu Val Val Ile
145                 150                 155                 160

Lys Gln Asn Gly Ala Val Ile Thr Asn Lys Gly Arg Lys Gln Ile Arg
            165                 170                 175

Glu Arg Gly Leu Ala Cys Phe Gln Asn Trp Val Glu Ala Ala Asp Val
            180                 185                 190

Phe Gln Asn Phe Ser Gly
            195
```

<210> SEQ ID NO 5
<211> LENGTH: 597
<212> TYPE: DNA
<213> ORGANISM: Mus musculus

<400> SEQUENCE: 5

```
atggtggacg tgctgggcgg gcggcgcctg gtgacccggg agggcacggt ggtggaggcc    60
gaggtggcgc tgcagaacaa ggtggtagct ttgtactttg cggcgggccg tgctcgccc    120
agccgcgact tcacgccgct gctctgcgac ttctacacgg agctggtgag cgaggcgcgg    180
cggcccgctc ccttcgaggt ggttttcgtg tcggcagacg gcagtgcgga ggagatgttg    240
gacttcatgc gcgagctgca cggctcctgg ctggcattgc ccttccacga ccctaccgg    300
caatctcaat gtgggccaat tccccgaat cttggtttca gcatccacgg ggctccggtc    360
tgccagcgtt ttctgccttt tacgattgga gtgtcaggaa ttcacatgtc tcaggagccc    420
caggactgtg aactgaagaa gaggtacgaa atcaccgcca tccccaagct ggtggtcatc    480
aagcagaacg gagctgtcat caccaacaaa gggcggaagc agatccgaga gcgcgggcta    540
gcttgctttc agaactgggt ggaagcagcc gatgttttcc aaaacttctc ggggtga      597
```